United States Patent
Bauer

(10) Patent No.: US 7,285,646 B2
(45) Date of Patent: Oct. 23, 2007

(54) ULTRAPURE TRANSFERRIN FOR PHARMACEUTICAL COMPOSITIONS

(75) Inventor: Shabtai Bauer, Jerusalem (IL)

(73) Assignee: Kamada Ltd., Rehovot (IL)

( * ) Notice: Subject to any disclaimer, the term of this patent is extended or adjusted under 35 U.S.C. 154(b) by 10 days.

(21) Appl. No.: 10/964,394

(22) Filed: Oct. 13, 2004

(65) Prior Publication Data

US 2005/0153875 A1    Jul. 14, 2005

Related U.S. Application Data

(63) Continuation of application No. PCT/IL02/00308, filed on Apr. 16, 2002.

(51) Int. Cl.
*C07K 14/79* (2006.01)
(52) U.S. Cl. .................... 530/394; 530/350; 514/2; 435/389
(58) Field of Classification Search ............. 530/350, 530/394; 514/2; 435/389
See application file for complete search history.

(56) References Cited

U.S. PATENT DOCUMENTS

| 4,841,026 A | 6/1989 | Van Beveren et al. ...... 530/394 |
| RE33,071 E * | 9/1989 | Stjernholm ................. 530/394 |
| 4,886,780 A | 12/1989 | Faulk ............................ 514/8 |
| 4,895,741 A | 1/1990 | Coffman ........................ 428/5 |
| 5,000,935 A | 3/1991 | Faulk ........................... 424/1.1 |
| 5,041,537 A | 8/1991 | Bethke et al. ................ 530/394 |
| 5,051,406 A * | 9/1991 | Satoh ........................... 514/21 |
| 5,252,715 A | 10/1993 | Haupt ........................ 530/394 |
| 5,744,586 A | 4/1998 | Rolf et al. ................... 530/394 |
| 5,792,645 A | 8/1998 | Beug et al. ................. 435/240 |
| 6,037,174 A * | 3/2000 | Smith et al. ................ 435/366 |
| 6,054,133 A | 4/2000 | Horwitz et al. ............ 424/248 |
| 6,251,860 B1 | 6/2001 | Parkkinen et al. ............. 514/8 |
| 6,299,878 B1 * | 10/2001 | Pierpaoli et al. ......... 424/184.1 |
| 6,326,473 B1 * | 12/2001 | Parkkinen et al. .......... 530/394 |
| 2002/0025318 A1 * | 2/2002 | Sparling et al. .......... 424/150.1 |
| 2003/0087450 A1 * | 5/2003 | Sundrehagen et al. ........ 436/87 |
| 2003/0229012 A1 * | 12/2003 | Thomas .......................... 514/6 |
| 2004/0014145 A1 * | 1/2004 | Althaus ....................... 435/7.1 |
| 2005/0054043 A1 * | 3/2005 | Funk et al. ................. 435/69.1 |
| 2005/0239137 A1 * | 10/2005 | Sundrehagen ............... 435/7.1 |

OTHER PUBLICATIONS van Gelder, W. (Comparative Biochemistry and Physiology, B: Biochemistry and Molecular Biology 111B(2), 171-9, 1995).*
Sandra Bear, William P. Steward, "Plasma Free Iron And Chemotherapy Toxicity", The LANCET, vol. 147, pp. 342-343 (1996).

* cited by examiner

*Primary Examiner*—David Lukton
(74) *Attorney, Agent, or Firm*—Winston & Strawn LLP

(57) ABSTRACT

The present invention relates to an ultrapure human transferrin, and to methods for manufacturing the ultrapure transferrin. The transferrin may be holo-, apo- or at any desired degree of iron saturation. The invention further relates to the use of ultrapure transferrin as the protein moiety of conjugates, and to pharmaceutical compositions comprising ultra transferrin alone as well as in the form of a conjugate.

50 Claims, 8 Drawing Sheets

Transferrin
Lot 411003

StdI StdII S1 S2

Transferrin
Lot 611003

StdI StdII S1 S2

FIG. 2 *(continued)*
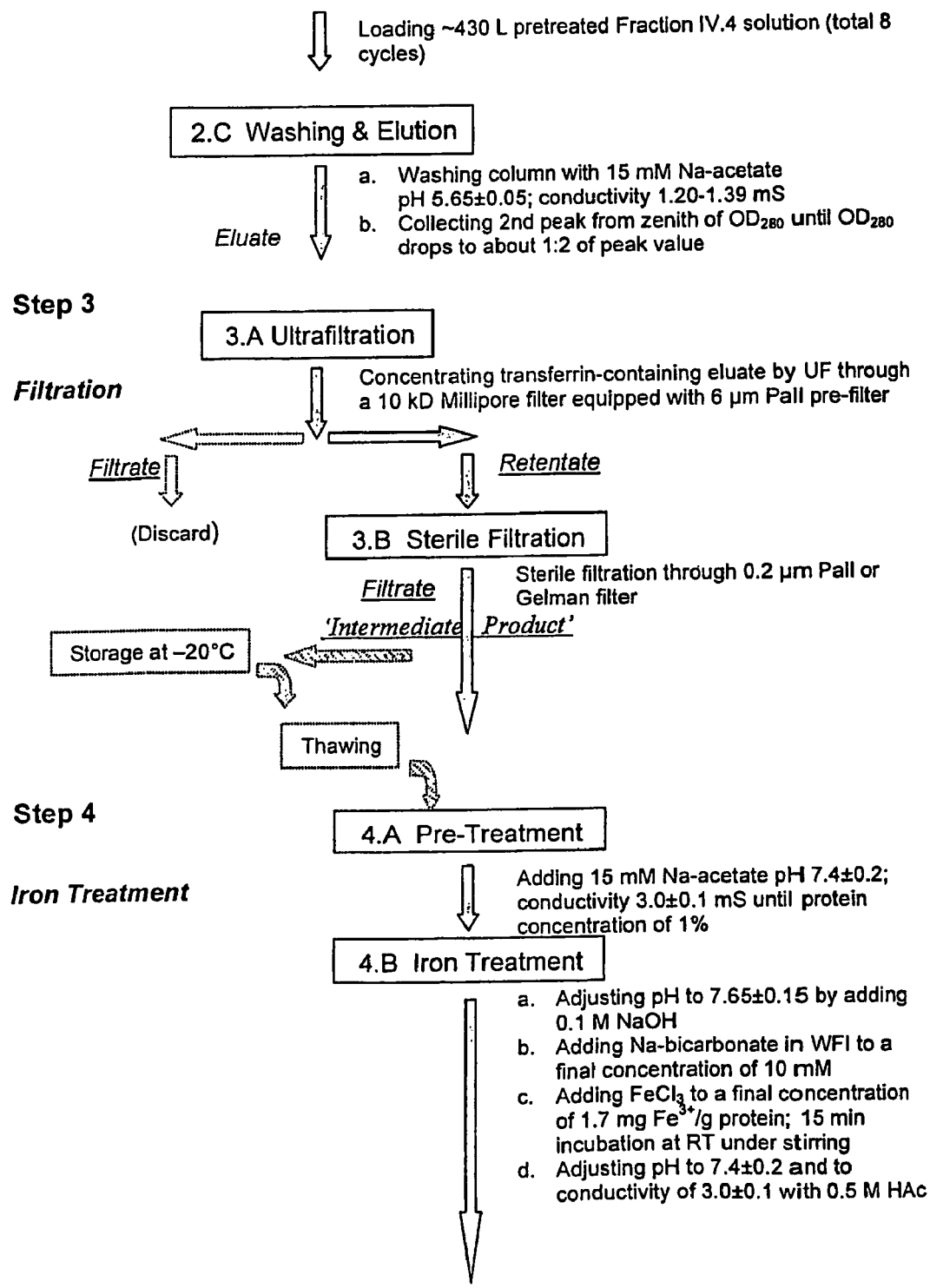

ULTRAPURE TRANSFERRIN FOR PHARMACEUTICAL COMPOSITIONS

CROSS-REFERENCE TO RELATED APPLICATIONS

This application is a continuation of International application PCT/IL02/00308 filed Apr. 16, 2002, the entire content of which is expressly incorporated herein by reference.

FIELD OF THE INVENTION

The present invention relates to an ultrapure human transferrin, and to a method for manufacturing the ultrapure transferrin. The invention further relates to the use of ultrapure transferrin as the protein moiety of conjugates, and to pharmaceutical compositions comprising ultra transferrin alone as well as in the form of a conjugate.

BACKGROUND OF THE INVENTION

Transferrin is an iron binding glycoprotein that transports iron in blood plasma and in the extracellular fluid of tissues. Transferrin binds two ferric ($Fe+3$) ions per molecule with high affinity, and normally all iron in plasma is bound to transferrin. The trivalent iron is delivered to the cell cytoplasm via transferrin receptors located on the cell surface. Apotransferrin is the iron-free transferrin; iron-saturated transferrin is referred to as Holotranferrin. As used in the present context, the term "transferrin" designates any form of transferrin, irrespective of its iron content.

Medical use of transferrin relates to the following main phenomena:

Pathological conditions in which the concentration of iron exceeds the iron binding capacity of transferrin, and non-transferrin-bound-iron can be detected in serum samples of the patients. Such pathological conditions include malignant neoplastic diseases, e.g. leukemia. The appearance of non-transferrin-bound-iron is particularly common during cytotoxic chemotherapy of malignant diseases (Reviewed in Bear and Steward, 1996 Lancet 347: 342-343). Transferrin may therefore be used for the prevention of the harmful effect of non-transferrin-bound-iron in patients (U.S. Pat. No. 6,251,860).

Transferrin receptors, located on the cell surface membrane, may be utilized for targeting compound into the cells, using transferrin-compound conjugates. It has been recently found that transferrin receptors are located on tumor cells, and therefore transferrin conjugates are designed for the diagnosis, imaging, localization and treatments of tumors (e.g. U.S. Pat. Nos. 5,000,935; 4,886,780; 4,895,741). Transferrin conjugates are also used for targeting nucleic acids into the cell (U.S. Pat. No. 5,792,645) and for the treatment of intracellular pathogens that reside in phagosomes (U.S. Pat. No. 6,054,133).

A growing need for serum-free cell culture media is raised by the pharmaceutical industry. Transferrin products are widely used as cell growth factors in such cultures.

Transferrin is also necessary as an additive to some cell cultures, including cultures of embryonic stem cells even in the presence of serum.

In any aspect of the pharmaceutical use, the transferrin to be used must meet high standards of purity and sterility, while maintaining maximum biological activity, designated by the iron-binding capacity.

Methods of obtaining purified, virally inactivated, non-toxic transferrin are known in the art U.S. Pat. No. 4,841,026 describes a method for viral inactivation using pasteurization for 10 hours at 60° C. As plasma proteins, including transferrin, are heat-sensitive they must be heat-inactivated in conjugation with stabilizers. The method disclosed therein therefore comprises the saturation of Cohn fraction containing transferrin with an excess of iron followed by the removal of free iron radicals and unwanted protein via filtration and ion exchange chromatography. The iron-saturated transferrin is then pasteurized. The method is therefore suitable only for the production of holo-transferrin; moreover, purity and bioactivity are not disclosed. In U.S. Pat. No. 5,252,715 a purified transferrin is pasteurized in the presence of complexing agent, and the complexing agent is removed with the bound iron, resulting in iron-free transferrin In this patent, aggregates produced during the heat treatment are removed by aluminum hydroxide, which is not desired in a preparation for pharmaceutical use.

U.S. Pat. No. 5,041,537 discloses a method of preparing high purity transferrin comprising the steps of precipitating the γ-globulins from the fraction containing the transferrin, removing the precipitate from residual liquid by ultrafiltration or gel filtration and concentrating the filtrate to the desired protein and ion concentration. Virus inactivation is obtained by a procedure that comprises UV radiation in the presence of β-propiolactone or treating the solution with specific detergent followed by ion-exchange chromatography. However, the transferrin obtained shows iron binding capacity of only about 80%. U.S. Pat. No. 5,744,586 describes a method for obtaining at least 95% pure transferrin. As described therein, a partially purified plasma fraction containing transferrin is concentrated and its ionic strength is reduced. The transferrin-containing fraction is chemically treated to inactivate enveloped viruses, and applied thereafter to an ion exchange medium in which the transferrin is adsorbed. The fraction comprising transferrin is then eluted from the ion exchange column and further nanofiltered to remove non-enveloped viruses.

U.S. Pat. No. 6,251,860 describes a pharmaceutical composition containing pure apotransferrin, having iron binding capacity of at least 90%, free from polymers and containing a maximum 3% of dimers. The method for virus inactivation includes two different ion exchange chromatography steps with solvent/detergent treatment, followed by filtration through a virus removal filter. Purity disclosed in this patent is at least 98%; however, purity is measured as the percentage of β-globulin and not as transferrin.

In summary, although prior art disclosures provide various methods for the production of transferrin, each method focuses on one or a few aspects of the product (purity, virus contamination, bioactivity, apo- or holo-transferrin etc.).

Therefore, there is a recognized need for, and it would be highly advantageous to have ultra-pure, virus safe, commercially reproducible, apo- and holo-transferrin.

SUMMARY OF THE INVENTION

It is an object of the present invention to provide an ultrapure human transferrin, suitable for use in pharmaceutical compositions for in vivo, ex vivo and in vitro applications. It is a further object of the present invention to provide a method of producing said ultrapure transferrin on a commercial scale in a commercially reproducible manner.

The present invention relates to human transferrin compositions, having the following characteristics: at least 99% purity, more preferably 99.1% purity, most preferably 99.5% purity, determined by the methods of electrophoresis on cellulose acetate membrane and/or HPLC using an ion exchange column; iron binding capacity of at least 1.0 mg/g protein, determined by titration; Negative for IgG, as determined by binding to anti Ig in 2% solution; non reactive with anti bovine transferrin antibodies, while reactive with anti human transferrin antibodies; non pyrogenic; free of pathogens as determined by known tests.

The ultrapure transferrin compositions of the present invention may be iron saturated (holo-), iron-free (apo-), or at any desired intermediate degree of iron saturation.

In one preferred embodiment, the present invention discloses iron saturated holo-transferrin at least 99% pure, more preferably 99.1% pure, most preferably 99.5% pure, with total iron-binding capacity of at least 1.0 mg/g protein and total iron bound of 1.2-1.7 mg/g; heat treated, sterile filtered and freeze dried, non-pyrogenic preparation; non-reactive with anti bovine transferrin antibodies; reactive with anti human transferrin antibodies; IgG free, free of viruses and mycoplasma and pink in color.

In yet another preferred embodiment, the present invention discloses iron saturated holo-transferrin at least 99% pure, more preferably 99.1% pure, most preferably 99.5% pure, with total iron-binding capacity of at least 1.0 mg/g protein and total iron bound of 1.2-1.7 mg/g protein; heat treated, sterile filtered non-pyrogenic solution, the pH of the solution is 6-8; non-reactive with anti bovine transferrin antibodies; reactive with anti human transferrin antibodies; IgG free, free of viruses and mycoplasma and deep red in color.

In yet another preferred embodiment the present invention discloses iron free, apo-transferrin at least 99% pure, more preferably 99.1% pure, most preferably 99.5% pure, with total iron binding capacity of at least 1 mg/g protein and total iron bound of not more than 30 µg/g protein; heat treated, sterile filtered and freeze dried non-pyrogenic preparation; non-reactive with anti bovine transferrin antibodies; reactive with anti human transferrin antibodies; IgG free, free of viruses and mycoplasma and off-white in color.

In yet another preferred embodiment the present invention discloses iron free, apo-transferrin at least 99% pure, more preferably 99.1% pure, most preferably 99.5% pure, with total iron binding capacity of at least 1 mg/g protein and total iron bound of not more than 30 µg/g protein; heat treated, sterile filtered non-pyrogenic solution; non-reactive with anti bovine transferrin antibodies; reactive with anti human transferrin antibodies; IgG free, free of viruses and mycoplasma and off-white in color.

It is another aspect of the present invention to provide a method of producing same ultrapure transferrin products on a commercial scale in a commercially reproducible manner.

The present invention further relates to a method of producing ultrapure transferrin from Cohn's fraction IV.4 or IV.1 paste, wherein the method comprises pre-treatment of the Cohn's fraction including thawing, treatment with Aerosil and PEG and pH adjustment. In one preferred embodiment, when the starting material is Cohn's fraction IV.4, the pre-treatment is completed by heat treatment followed by dilution and centrifugation. In another preferred embodiment, when the starting material is Cohn's fraction IV.1, the pre-treatment is completed by conductivity adjustment and centrifugation. The resulted supernatant is then filtered, and after pH re-adjustment, is subjected to a first DEAE Sepharose fast flow anion exchange chromatography. In one preferred embodiment, when the starting material is Cohn's fraction IV.4, the transferrin containing eluate is concentrated by ultra-filtration and sterile-filtered through 0.2 µm filter. At this stage the product may be stored at −20° C. before further treatment. If such storage is undertaken, the product should be thawed before the next step of iron treatment.

In another preferred embodiment, when the starting material is Cohn's fraction IV.1, the transferrin containing eluate is subjected to CM-Sepharose fast flow cation exchange chromatography and the eluate of this column is collected for the iron treatment in which transferrin is saturated with iron.

The iron-saturated transferrin solution (derived from pre-treated Cohn's fraction IV.4 or IV.1) is then subjected to a second DEAE Sepharose fast flow anion exchange chromatography. The transferrin containing protein eluted from the column is concentrated by ultra-filtration, sterilized by 0.2 µm and 0.1 µm filtration and remaining viruses are inactivated. In one preferred embodiment, virus inactivation is performed by pasteurizing for about 11 h at 60.0±0.5° C.

In one preferred embodiment, the sterile, virus inactivated, ultrapure holo-transferrin is lyophilized. The lyophilized product can be re-constituted at a later time.

In yet another preferred embodiment, the sterile, virus inactivated ultrapure holo-transferrin is subjected to iron removal by diafiltration against water until conductivity is not more than 1 mS and sodium ion concentration is not more than 10 mEq/ml. After pH adjustment, ultra filtration and sterile filtration through a 0.2 µm pore size filter, ultra-pure apo-transferrin solution is obtained. In one preferred embodiment, the ultra-pure apo-transferrin is lyophilized. The lyophilized product can be re-constituted as required at a later time.

In yet another aspect, the present invention relates to the above-defined ultrapure transferrin product as the protein moiety for drug conjugates, to be used for targeting the conjugated moiety to transferrin receptors located on the cell surface.

The present invention also relates to pharmaceutical compositions comprising as an active ingredient ultrapure transferrin or transferrin conjugates, further comprising a pharmaceutically acceptable diluent or carrier.

DETAILED DESCRIPTION OF THE INVENTION

Figure 1A:
FIG. 1A shows a cellulose acetate electrophoresis of ultrapure transferrin.

It is an object of the present invention to provide an ultrapure human transferrin, characterized by having at least 99% purity, more preferably 99.1% purity, most preferably 99.5% purity, iron-binding capacity of at least 1.0 mg/g protein, non-pyrogenic, IgG free, and pathogen free. It is a further object of the present invention to provide a method of producing said ultrapure transferrin on a commercial scale in a commercially reproducible manner.

The present invention relates to ultrapure transferrin products, produced from human plasma which is non-reactive for Hepatitis B surface Antigen (HbsAg), antibody to HIV I+II, anti-HCV and Syphilis, as determined by tests known in the art, having the characteristics of: at least 99% purity, more preferably 99.1% purity, most preferably 99.5% purity determined by the methods of electrophoresis on cellulose membrane and HPLC using ion exchange column; iron binding capacity of not less than 1.0 mg/g protein, determined by titration; negative for IgG, as determined by binding to anti Ig in 2% solution; non-reactive with anti-bovine transferrin antibodies; reactive with anti human transferrin antibodies; essentially free of bacterial endotoxins (<1 EU/mg) and free of detectable mycoplasma after growth for 4 weeks.

The present invention also relates to pharmaceutical compositions comprising as an active ingredient ultrapure transferrin or transferrin conjugates, further comprising a pharmaceutically acceptable diluent or carrier.

As used herein, a "pharmaceutical composition" refers to a preparation with one or more of the compounds described herein, or physiologically acceptable salts thereof, together with other chemicals components such as physiological acceptable diluents or carriers. The purpose of a pharmaceutical composition is to facilitate administration of a compound to an organism.

Pharmaceutical compositions according to the present invention may be manufactured by processes well known in the art, e.g. by means of conventional mixing, dissolving, granulating, grinding, pulverizing, dragee-making, levigating, emulsifying, encapsulating, entrapping or lyophilizing processes.

Pharmaceutical composition for use in accordance with the present invention thus may be formulated in a conventional manner using one or more acceptable diluents or carriers comprising excipients and auxiliaries, which facilitate processing of the active compounds into preparations, which can be used pharmaceutically.

More particularly the present invention relates to pharmaceutical compositions for parenteral administration. Pharmaceutical compositions for parenteral administration are formulated for intravenous injections, intravenous infusion, intradermal, intralesional, intramuscular, and subcutaneous injections or depots; or they may be administered parenterally by means other than injection, for example, they could be introduced laparascopically, intravesicularly, or via any orifice not related to the gastrointestinal tract.

In another aspect the present invention relates to a method comprising the step of administering to a subject in need thereof a therapeutically effective amount of the above-identified ultrapure transferrin.

In yet another aspect the present invention relates to a method comprising the step of administering to a subject in need thereof a therapeutically effective amount of transferrin conjugate.

Preferred Embodiments

In one preferred embodiment, the present invention discloses iron-saturated holo-transferrin at least 99% pure, more preferably 99.1% pure, most preferably 99.5% pure, with total iron-binding capacity of at least 1.0 mg/g protein and total iron bound of 1.2-1.7 mg/g; heat treated, sterile filtered and freeze dried, non-pyrogenic preparation; IgG free, non-reactive with anti-bovine transferrin antibodies, reactive with anti-human transferrin antibodies; essentially free of bacterial endotoxins, free of viruses and mycoplasma and pink in color. The water content of the product is not more than 3.0%, and the protein content on a dry weight basis is at least 98%, more preferably at least 99%. In addition to the iron binding capacity, the biological efficacy of the holo transferrin is measured as stimulating hybridoma cell growth.

In yet another preferred embodiment, the present invention discloses iron saturated holo-transferrin at least 99% pure, more preferably 99.1% pure, most preferably 99.5% pure, with total iron-binding capacity of at least 1.0 mg/g protein and total iron bound of 1.2-1.7 mg/g protein; heat treated, sterile filtered non-pyrogenic solution, the pH of the solution is 6-8; IgG free, non-reactive with anti-bovine transferrin antibodies, reactive with anti-human transferrin antibodies; essentially free of bacterial endotoxins, free of viruses and mycoplasma and deep red in color. In addition to the iron binding capacity, the biological efficacy of the holo transferrin is measured as stimulating hybridoma cell growth.

In yet another preferred embodiment the present invention discloses iron free, apo-transferrin at least 99% pure, more preferably 99.1% pure, most preferably 99.5% pure with total iron binding capacity of at least 1 mg/g protein and total iron bound of not more than 30 μg/g protein; heat treated, sterile filtered, freeze dried non-pyrogenic preparation; IgG free, non-reactive with anti bovine transferrin antibodies, reactive with anti human transferrin antibodies; essentially free of bacterial endotoxins, free of viruses and mycoplasma and off-white in color. The water content of the product is not more than 3.0%, and the protein content on a dry weight basis is at least 98%, more preferably at least 99%. In addition to the iron binding capacity, the biological efficacy of the apo-transferrin is measured as stimulating hybridoma cell growth.

In yet another preferred embodiment the present invention discloses iron free, apo-transferrin at least 99% pure, more preferably 99.1% pure, most preferably 99.5% pure with total iron binding capacity of at least 1 mg/g protein and total iron bound of not more than 30 μg/g protein; heat treated, sterile filtered non-pyrogenic solution; IgG free, non-reactive with anti bovine transferrin antibodies, reactive with anti human transferrin antibodies; essentially free of bacterial endotoxins, free of viruses and mycoplasma and off-white in color. The water content of the product is not more than 3.0%, and the protein content on a dry weight basis is at least 98%, more preferably at least 99%. In addition to the iron binding capacity, the biological efficacy of the apo-transferrin is measured as stimulating hybridoma cell growth.

In another aspect the present invention discloses a method of producing ultrapure transferrin products on a commercial scale in a commercially reproducible manner.

The starting material of the present invention may be a paste of Cohn's fraction number IV.4 or IV.1. General methods like pH measurements, pH adjustment, resin washes etc. may be performed by any one of the common methods known in the art. In one preferred embodiment the starting material is paste of Cohn's fraction number IV.4, wherein the required and optimal process steps of the present invention are as follows:

1. Pretreatment of Cohn's fraction IV.4 paste, which is stored frozen. At this pretreatment stage, pure water as referred to herein is reverse osmosis water. The pretreatment includes:
   1.1. Thawing. In a preferred embodiment, thawing is performed at 15-25° C., at a time duration related to the amount to be thawed.
   1.2. Treatment with Polyethylene glycol (PEG) and Aerosil. In a preferred embodiment, the Polyethylene glycol added is PEG 4000.
   1.3. pH adjustment In a preferred embodiment, the pH is adjusted with acetic acid to pH 5.25-5.35, and than the solution is diluted by pure water.

1.4. Heat treatment In a preferred embodiment, the solution is heated to 52-54° C. for about 3 h; the solution is then cooled below 30° C.

1.5. Centrifugation. In a preferred embodiment, centrifugation is performed by separating centrifuge. In a more preferred embodiment, the ratio of solution: pure water is at about 1:0.83. Sludge is discarded and the supernatant is taken for next step.

1.6. Filtration and pH adjustment. En a preferred embodiment, the supernatant is filtered through a 3 μm filter, and the pH is adjusted to 5.55-5.85 with a solution of sodium hydroxide.

From this step on, pure water is referred herein as water for injection.

2. First anion exchange chromatography. The pre-treated Cohn's fraction IV.4 is loaded on anion-exchange column wherein the transferrin is adsorbed onto the anion-exchange resin, and is then eluted by salt-containing solution. In a preferred embodiment, the anion-exchange resin is DEAE Sepharose fast flow, equilibrated with sodium acetate. In a more preferred embodiment, the DEAE column is washed with Na acetate, and then equilibrated with Na acetate solution at pH of 5.6-5.7 and conductivity of 1.2-1.39 mS. In the same preferred embodiment the pre-treated Cohn's fraction IV.4 is loaded onto the DEAE column; the column is washed with sodium acetate solution, more preferably with 15 mM Na-acetate at pH 5.6-5.7, conductivity 1.2-1.39 mS, and the second $OD_{280}$ peak of the eluate is collected until $OD_{280}$ drops to about 1:2 of peak value.

3. Concentration. The transferrin-containing eluate is then concentrated. In a preferred embodiment, concentration is performed by tangential ultra-filtration. In a more preferred embodiment, the ultra-filtration is performed through a 10 kD Millipore filter. In a most preferred embodiment, the ultra-filtration is performed through a 10 kD Millipore filter equipped with a 6 μM pre-filter.

4. Sterilization. The concentrated transferrin-containing solution is filter-sterilized. In a preferred embodiment, the sterilization filter has a 0.2 μm pore size.

5. Optional storage. The filter-sterilized, concentrated intermediate product may be stored at −20° C. If such storage takes place, the product should be thawed before the iron treatment. In a preferred embodiment, thawing is performed at 15-25° C., at a time duration related to the amount to be thawed.

6. Iron treatment. The end product of the process described herein can be holo- or apo-transferrin. An iron-saturation step is employed in both paths. Iron saturation is achieved by the addition of $FeCl_3$. In a preferred embodiment, the protein concentration of the concentrated intermediate product is brought to 1%, pH and conductivity are adjusted and $FeCl_3$ is added to a final concentration of 1.7 mg $Fe^{+3}$/g protein. In a more preferred embodiment, Na-acetate solution of 15 mM, pH 7.2-7.6 and conductivity 2.9-3.1 mS is added until the protein concentration of the concentrated intermediate product is 1%. The pH is further adjusted to 7.5-7.8 by sodium hydroxide. Sodium bicarbonate in pure water is added to a final concentration of 10 mM and $FeCl_3$ is added to a final concentration of 1.7 mg $Fe^{+3}$/g protein. The solution is incubated for 15 min with stirring, after which the pH is adjusted to 7.2-7.6 and the conductivity to 2.9-3.1 mS.

7. Second anion exchange chromatography. The iron-treated solution is loaded on an anion-exchange column wherein the transferrin is adsorbed onto the anion-exchange resin, and is then eluted by a salt-containing solution. In a preferred embodiment, the anion-exchange resin is DEAE Sepharose fast flow, equilibrated with sodium acetate. In a more preferred embodiment, after several subsequent washes, the column is equilibrated by sodium acetate solution at pH of 7.2-7.6 and at conductivity of 2.9-3.1 mS. In the same preferred embodiment the iron-treated solution is loaded onto the DEAE column; the column is washed with sodium acetate solution, more preferably with Na-acetate at pH 7.2-7.6, conductivity 2.9-3.1 mS, until close to the $OD_{280}$ baseline. The transferrin-containing protein is eluted with Na acetate at pH 7.2-7.6, conductivity 5.4-5.6; collection starts as soon as the $OD_{280}$ peak appears until the OD drops to 25% of the peak height value.

8. Second concentration. The iron-saturated, transferrin-containing solution is then concentrated. In a preferred embodiment, concentration is performed by ultra-filtration. In more preferred embodiment, the ultra-filtration is performed through a 10 kD Millipore filter. In a most preferred embodiment, the ultra-filtration is performed through a 10 kD Millipore filter equipped with a 6 μm pre-filter, until the solution reaches approximately 15% of its initial volume.

9. Filter sterilization. In a preferred embodiment, the sterile filtration is done using 0.2 μm and 0.1 μm filters.

10. Virus inactivation by one or more methods known in the art. In one preferred embodiment, virus inactivation is performed by pasteurization. In a more preferred embodiment, pasteurization is performed by heating the filter-sterilized solution for about 11 h at 59-61° C.

After this stage, in which ultrapure transferrin solution is obtained, the method steps are selected according to the final product, selected from a group consisting of holo-transferrin in solution, lyophilized holo-transferrin, apo-transferrin in solution and lyophilized apo-transferrin.

For obtaining holo-transferrin in solution, the solution is diluted with pure (injection grade) water to obtain the required transferrin concentration. In one preferred embodiment, the transferrin concentration in solution is 5% (w/v).

For obtaining lyophilized holo-transferrin, the sterilized solution is subjected to lyophilization. In a preferred embodiment, the lyophilization is performed for 48-96 h. In more preferred embodiment, lyophilization is performed until the water content is not more that 3.0%.

For obtaining lyophilized apo-transferrin the following required and optimal process steps are taken:

11. Iron removal. Iron is removed by diafiltration against sodium citrate, followed by diafiltration against pure water. In a preferred embodiment, iron removal is done by diafiltration through a 10 kD Millipore filter equipped with a 6 μm pre-filter, against 200 mM sodium citrate at a pH of 4.4-4.5, until the iron concentration is not more than 30 μg/mg protein. The solution pH is adjusted to 7.5-7.8 by sodium hydroxide, and the solution is diluted with pure water. A second diafiltration is then performed against pure water until the conductivity is below 1 mS and the sodium concentration is below 10 mEq/ml.

12. Concentration. The apo-transferrin containing solution is then concentrated. In a preferred embodiment, concentration is performed by ultra-filtration through 10 kD Millipore filter equipped with a 6 μm pre-filter, until the total weight reaches about 25% of the initial weight.

13. Sterilization. The pure apo-transferrin solution is sterilized by filtration. In a preferred embodiment, the filtration is through a 0.2 μm filter.

14. Lyophilization. Final ultra-pure apotransferrin is achieved after lyophilization. In a preferred embodiment, lyophilization is performed for 48-96 h. In a more preferred embodiment, lyophilization is performed until the water content is not more than 3.0%.

In another preferred embodiment the starting material is paste of Cohn's fraction number IV.1, wherein the required and optimal process steps of the present invention are as follows:

1. Pretreatment of Cohn's fraction IV.1 paste, which is stored frozen. The pretreatment includes:
   1.1. Thawing. In a preferred embodiment, thawing is performed by re-suspension of the paste in pure (injection grade) water at an amount related to the amount to be thawed, adjusting the pH to 8.95-9.45 with sodium hydroxide.
   1.2. Treatment with Aerosil. In a preferred embodiment, Aerosil is added at 7.8-8.2% w/w paste, and the suspension is incubated for 90-110 min. at 38° C. The suspension is then cooled to 20-25° C.
   1.3. Treatment with Polyethylene glycol (PEG). In a preferred embodiment, the polyethylene glycol is PEG 4000. In a more preferred embodiment, the pH of the suspension is adjusted to 5.7-6.3 by acetic acid. PEG 4000 is then added at 10.5-11.5% w/v, and the conductivity is adjusted to 2.7-3.3 mS with NaCl.
   1.4. Centrifugation. In a preferred embodiment, centrifugation is performed by separating centrifugation. The sludge is discarded and the supernatant is taken for next step.
   1.5. Filtration. In a preferred embodiment, the supernatant is filtered through a 1 μm depth filter.
2. First anion exchange chromatography. The pre-treated Cohn's fraction IV.1 is loaded on an anion-exchange column wherein the transferrin containing protein is collected from the wash. In a preferred embodiment, the anion-exchange resin is DEAE Sepharose fast flow, equilibrated with sodium acetate. In a more preferred embodiment, the sodium acetate solution for column equilibration is at a pH of 5.9-6.0 and conductivity of 2.9-3.1 mS. In the same preferred embodiment the pre-treated Cohn's fraction IV.1 is loaded onto the DEAE column; the column is washed with sodium acetate solution, more preferably with Na-acetate at pH 5.9-6.0, conductivity 2.0-2.2 mS, followed by a wash with Na-acetate at pH 5.9-6.0, conductivity 2.9-3.1. The transferrin-containing protein in the wash fluid is collected from the beginning of the first peak until the second flow-trough peak reaches its top. In still the same preferred embodiment the pH is adjusted by addition of sodium acetate and 5% acetic acid and/or 0.5N sodium hydroxide the pH is adjusted to 5.4-5.5 and the conductivity to 7.9-8.1 mS.
3. Cation exchange chromatography. The transferrin-containing solution is then loaded on a cation exchange column wherein the transferrin is adsorbed onto the cation-exchange resin, and is then eluted by a salt-containing solution. In a preferred embodiment, the cation exchange column is CM-Sepharose fast flow. In a more preferred embodiment, after adequate washing, the CM-Sepharose column is equilibrated with Na acetate at pH 5.3-5.4, conductivity 0.9-1.0 mS. The transferrin-containing solution is then loaded, the column is washed with Na acetate at pH 5.3-5.4, conductivity 0.9-1.0 mS, and the protein is eluted with Na acetate at pH 6.1-6.3, conductivity 8.8-9.0 mS, until the $OD_{280}$ drops below 25% of the peak height value.
4. Iron treatment The end product of the process described herein can be holo- or apo-transferrin. An iron-saturation step is employed in both paths. Iron saturation is achieved by the addition of $FeCl_3$. In a preferred embodiment, the transferrin-containing protein solution pH is adjusted to 7.5-7.8 by sodium hydroxide. In the same preferred embodiment, sodium bicarbonate in pure (injection grade) water is added to a final concentration of 10 mM, and $FeCl_3$ is added to a final concentration of 1.7 mg $Fe^{+3}$/g protein. The solution is incubated for 15 min under stirring; the solution pH is then adjusted to 5.9-6.1 and its conductivity to 2.9-3.1 mS, and the solution is incubated for an additional 15 min.

Second anion exchange chromatography, concentration and sterilization of the above-obtained transferrin-containing protein are performed with minor modifications in accordance with steps 7-10 above. The end products of holo- and apo-transferrin are obtained in accordance to steps 11-14 above.

In yet another aspect, the present invention relates to the above-defined ultrapure transferrin products as the protein moiety in conjugates, to be used for targeting the conjugated moiety to transferrin receptors located on the cell surface. The conjugated moiety can be selected from, but not restricted to, the group consisting of a cytotoxic compound, a cytostatic compound, an antisense compound, an anti-viral agent, a specific antibody, an imaging agent and a biodegradable carrier. Conjugates may be produced in any suitable method known in the art.

The present invention is further illustrated by the following non-limiting examples.

EXAMPLES

Example 1

Characterization of the Ultrapure Transferrin Product Obtained by the Method of the Present Invention As will be recognized by those skilled in the art, and as shown in the above-described examples, the method disclosed in the present invention for the production of holo- and apo-transferrin is commercially feasible and simple. The process is also highly reproducible, as illustrated in the following table 1. Table 1 shows the product specifications, and the results obtained for 4 independent batches. Two of the batches are of holo- and two of apo-transferrin; however, since the majority of the process steps are identical for both, all the four could be considered except for the iron content. In the present example, all batches are lyophilized.

TABLE 1

| TEST | SPECIFICATION | RESULTS |
| --- | --- | --- |
| Appearance | White, lyophilized powder (apo-transferrin) | White, lyophilized powder |

TABLE 1-continued

| TEST | SPECIFICATION | RESULTS |
| --- | --- | --- |
|  | Reddish, lyophilized powder (holo-transferrin) | Reddish, lyophilized powder |
| Solubility | Readily soluble at 1% in water | Readily soluble |
| pH (3% solution) | 7.0-8.0 | 7.4, 7.4, 7.1, 7.3 |
| pH (1% solution) | 6.5-8.0 | 7.2, 7.2 |
| Water content (for lyophilized products) | Not More Than (NMT) 3.0% | 2.4, 2.5, 2.0, 3.0 |
| Protein content | Not Less Than (NLT) 98% (dry basis) | 99, 100, 99.3, 99.3 |
| Electrophoretic purity (cellulose acetate) | NLT 99% | 100, 100, 99.6, 100 |
| Chromatography purity (HPLC) | NLT 99% | 99, 99.3, 100, 99.2 |
| Total bound iron | NMT 0.03 mg/g protein (for apo-transferrin) | 0.03, <001 |
|  | 1.2-1.7 mg/g protein (for holo-transferrin) | 1.2, 1.3 |
| Total binding iron capacity | NLT 1.0 mg/g | 1.2, 1.3, 1.2, 1.3 |
| Total aerobic plate count | For information only (CFU/g) | <7, <7, <7, |
| Bacterial Endotoxin (LAL) | NMT 1.0 EU/mg | <0.005, <0.005, <0.005, <0.005, |
| Protein identity | Anti Human: reactive | Human: (+), (+), (+), (+) |
|  | Anti Bovine: non reactive | Bovine: (−), (−), (−), (−) |
| Spectral analysis | UV absorption max. 280 nm | Pass, Pass, Pass, Pass |
| IgG free | Negative (at 2%) for anti-IgG | (−), (−), (−), (−) |
| Mycoplasma | No mycoplasma growth for 4 weeks | Pass, Pass, Pass, Pass |
| Biological efficacy | Stimulate cell growth* (25 μg/ml) | Pass, Pass, Pass, Pass |

*3 hybridoma cell types from the following parent myelomas: SP 2/0-Ag14, P3X63Ag8-653.

Figure 1A:
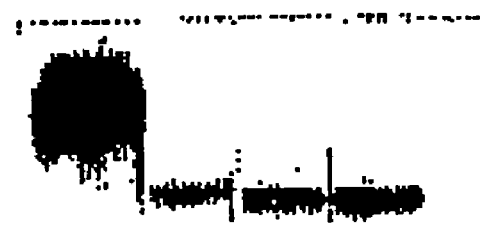
Figure 1B:
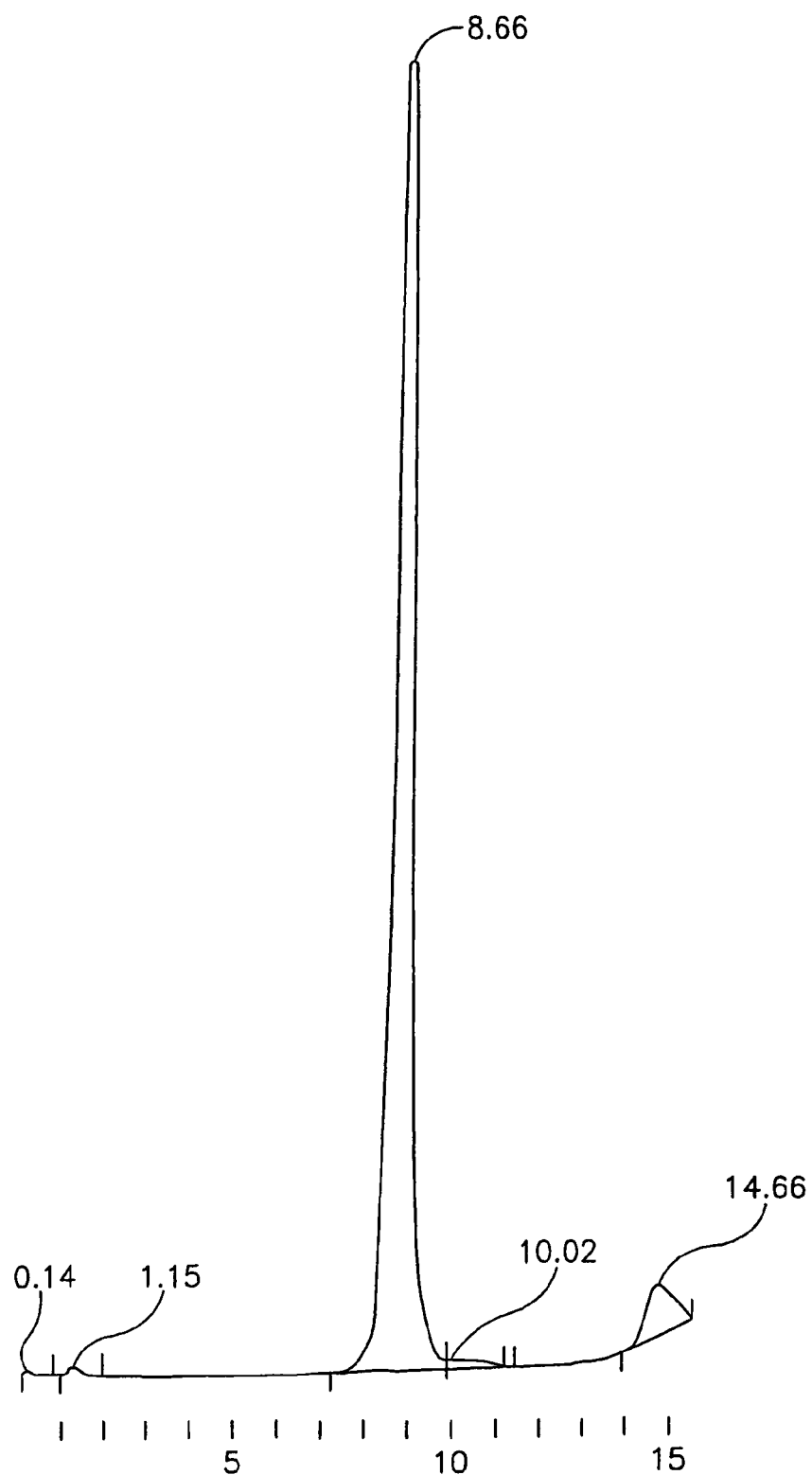
FIG. 1B shows HPLC chromatogram of ultrapure transferrin.

The purity of the resulted transferrin is at least 99%, as shown in FIG. 1. Purity was determined by electrophoresis on cellulose acetate (FIG. 1A) and by HPLC (FIG. 1B). Electrophoresis was performed on cellulose acetate membrane. After protein separation, proteins were stained with Red Ponceau S for detection. HPLC was performed with Mono-Q anion exchange column, at room temperature, flow rate of 0.8 ml/min. by linear gradient of conductivity.

Example 2

Obtaining Transferrin-Containing Protein Solution Form Cohn's Fraction IV.4 and IV.1

Figure 2:
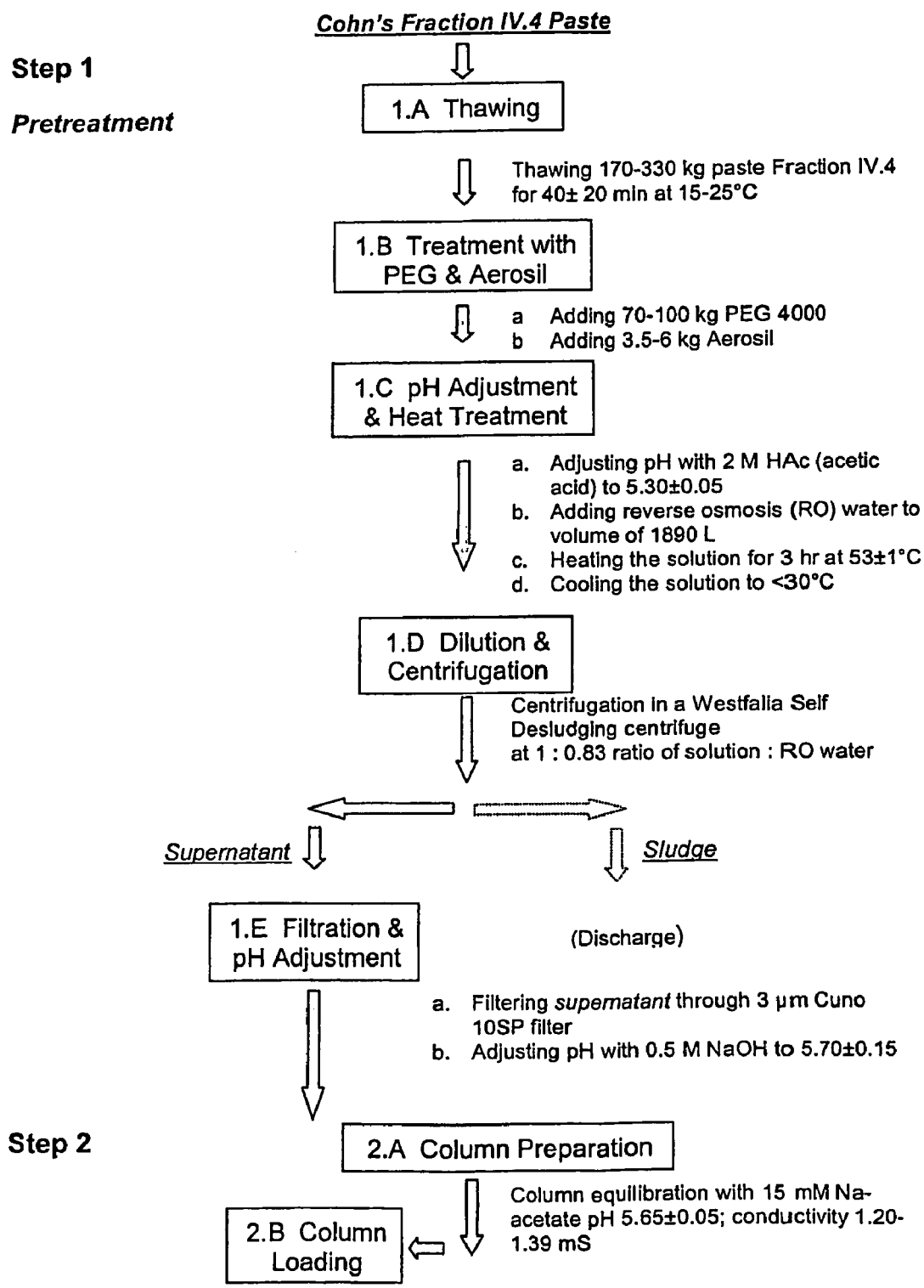
FIG. 2 shows a transferrin manufacturing process flow chart starting from Cohn's fraction IV.4
Figure 2:
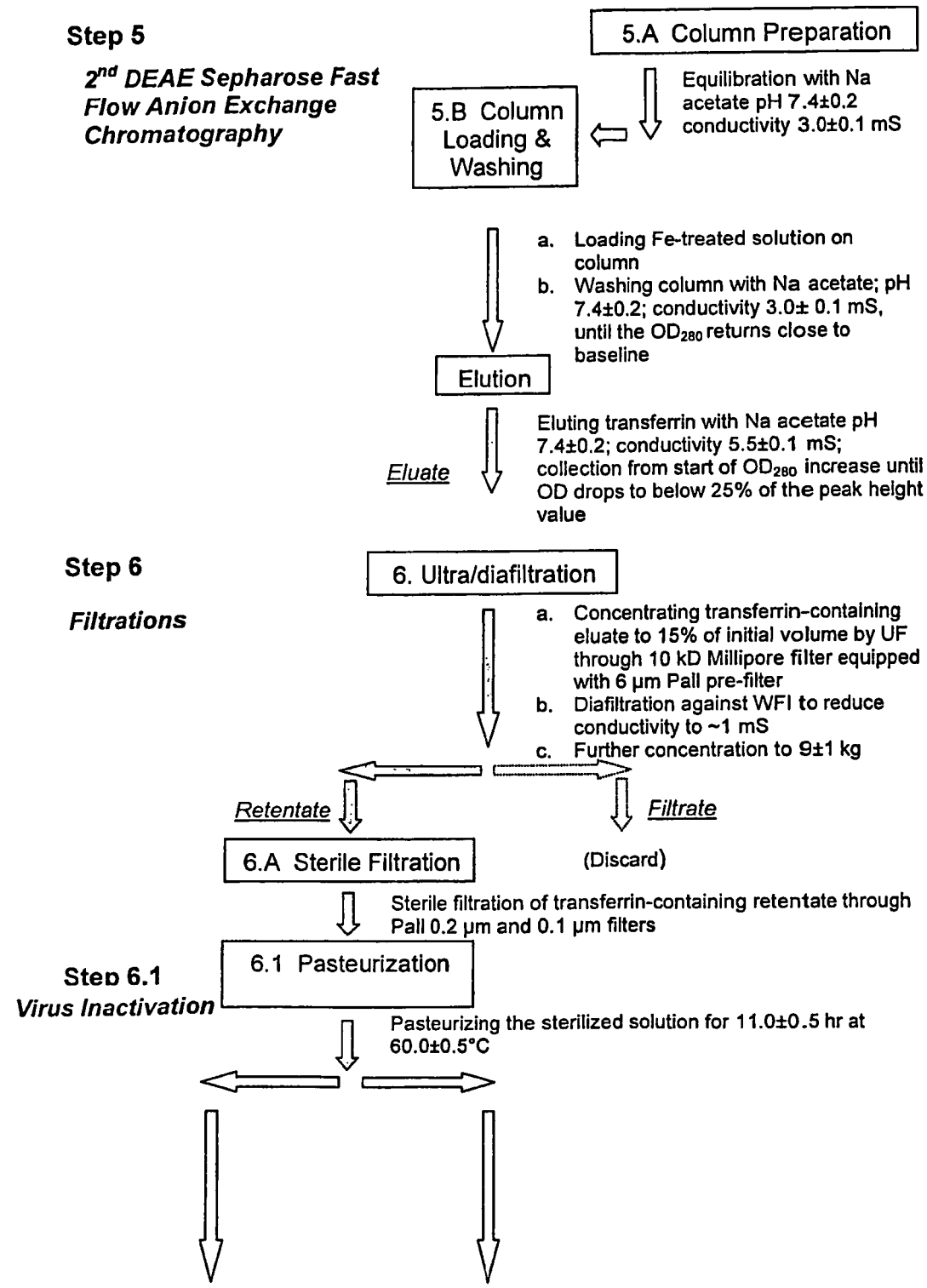
Figure 2:
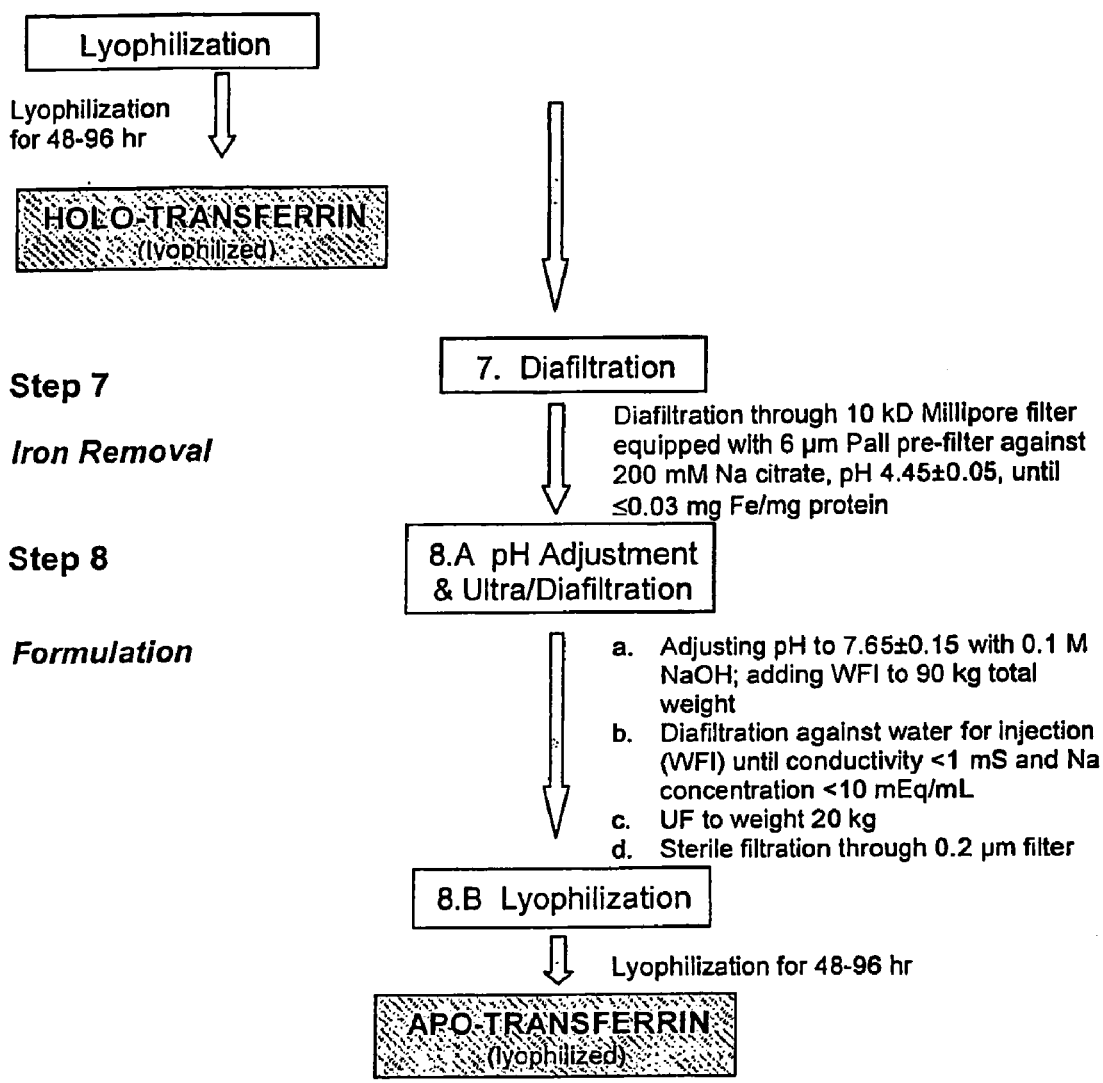
Figure 3:
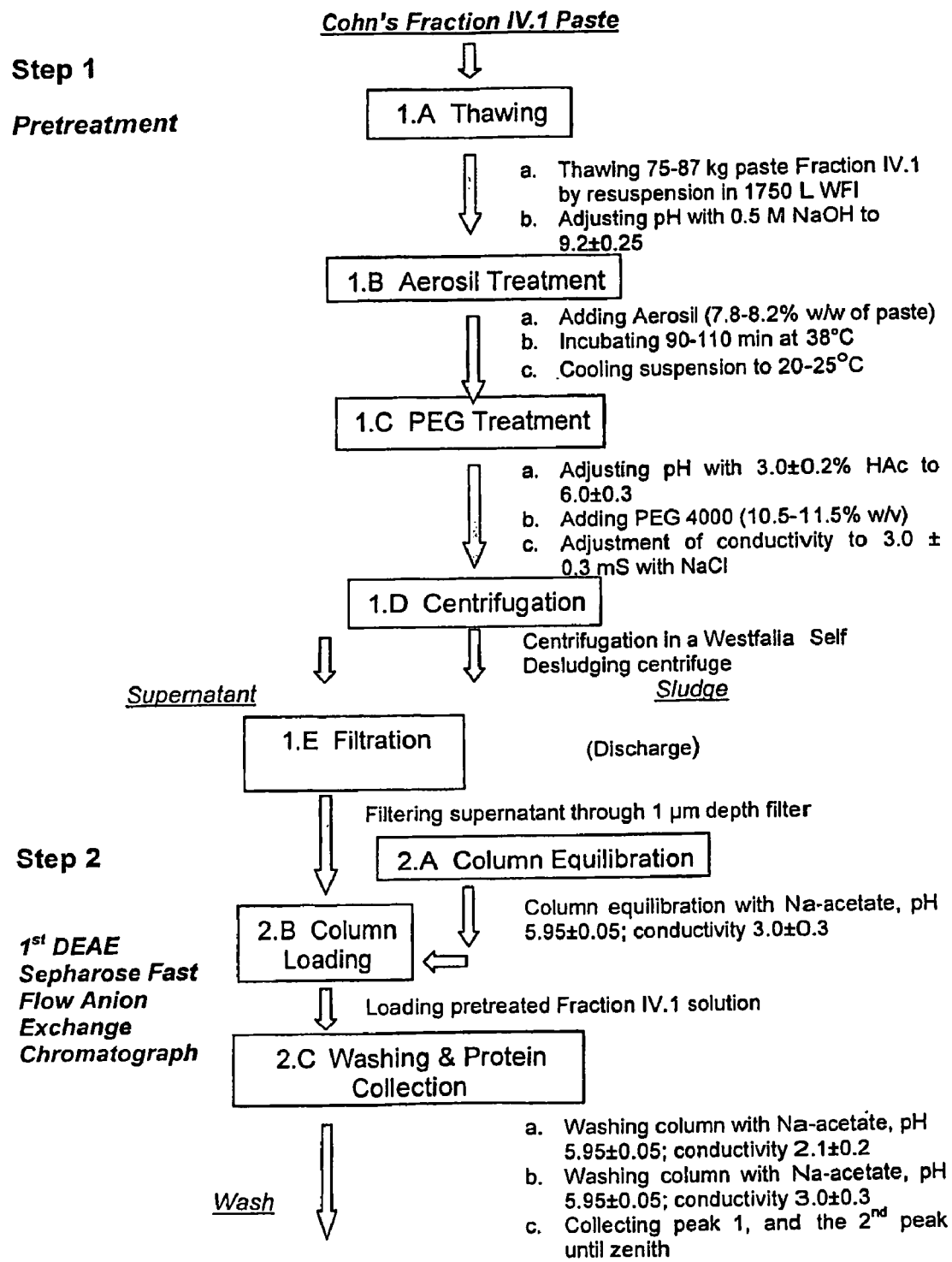
FIG. 3 shows a transferrin manufacturing process flow chart starting from Cohn's fraction IV.1
Figure 3:
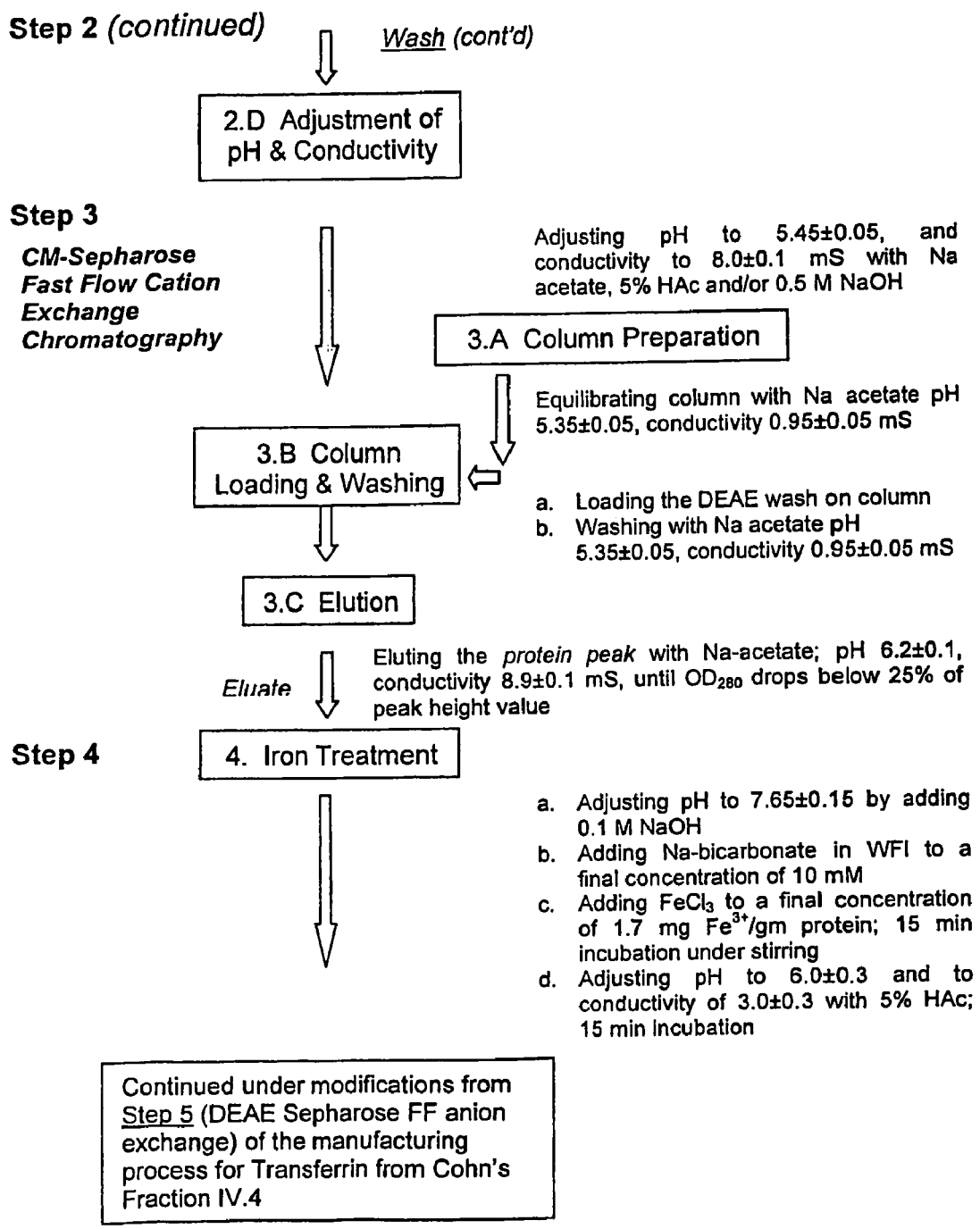

By the method of the present invention, ultrapure transferrin can be produced either from Cohn's fraction IV.1 and IV.4. The processes according to the present invention are as follows:

A. Obtaining Transferrin-Containing Protein Solution from Cohn's Fraction IV.4 (Summarized in FIG. 2A)

170-330 Kg paste fraction IV.4 was thawed at 15-25° C. for 20-60 min. 70-100 kg PEG 4000 was added, together with 3.5-6.0 kg of Aerosil. The suspension pH was then adjusted to 5.25-5.35 with 2 M acetic acid, and it was diluted by the addition of 1890-liter reverse-osmosis water. The solution was heated at 52-54° C. for 3 h, and then cooled to below 30° C. After cooling, the solution Was centrifuged in a Westfalia Self Desludging centrifuge at 550-750 liter/h, and ratio of solution: reverse osmosis water of 1:0.83. Sludge was discarded; the supernatant was filtered through a 3 μm Cuno 10SP filter, and its pH was adjusted to 5.55-5.85 with 0.5 N NaOH.

The filtered solution (approximately 430 liters of the pretreated fraction IV.4 supernatant) was then loaded on DEAE Sepharose fast flow anion exchange column, equilibrated with 15 mM Na-acetate at pH 5.6-5.7, conductivity 1.20-1.39 mS. The column was then washed with 15 mM Na-acetate at pH 5.6-5.7, conductivity 1.20-1.39 mS. The eluate, was collected starting at the top of the second $OD_{280}$ peak until the $OD_{280}$ drops to about 1:2 of peak value. The transferrin-containing eluate was then concentrated by ultrafiltration using a 10 kD Millipore filter equipped with 6 μm Pall pre-filter.

The concentrated transferrin-containing solution was then filter-sterilized by filtering through a filter of 0.2 μm (Pall or Gelman). The filter-sterilized, concentrated intermediate product may be stored at −20° C. If such storage takes place, the product should be thawed at 15-25° C. before the iron treatment for time duration relative to the amount to be thawed. After purifying the transferrin, an iron-saturation step was employed. Iron saturation was achieved by the addition of $FeCl_3$, as follows: the protein concentration of the concentrated intermediate product was brought to 1%, by Na-acetate solution of 15 mM, pH 7.2-7.6 and conductivity 2.9-3.1 mS. The pH was then further adjusted to 7.5-7.8 by 0.1 M NaOH. Sodium bicarbonate in pure (injection grade) water was added to a final concentration of 10 mM and $FeCl_3$ was added to a final concentration of 1.7 mg $Fe^{+3}$/g protein. The solution was incubated for 15 min with stirring, after which the pH was adjusted to 7.2-7.6 and the conductivity to 2.9-3.1 mS with 0.5 M acetic acid. The iron content for the iron-saturated, holo-transferrin final product was 1.2-1.7 mg/g.

The iron-treated solution was loaded on an anion-exchange column wherein the transferrin was adsorbed onto the anion-exchange resin, and was then eluted by salt-containing solution. The DEAE Sepharose fast flow anion-exchange resin was equilibrated with sodium acetate solution at pH of 7.2-7.6, conductivity of 2.9-3.1 mS. The iron-treated solution was then loaded onto the DEAE column; the column was washed with sodium acetate solution at pH 7.2-7.6, conductivity 2.9-3.1 mS, until close to the $OD_{280}$ baseline. Transferrin was eluted with Na acetate at pH 7.2-7.6, conductivity 5.4-5.6; collection started as soon as the $OD_{280}$ peak appeared until the OD droped to 25% of the peak height value.

B. Obtaining Transferrin-Containing Protein Solution from Cohn's Fraction IV.1 (Summarized in FIG. 2B)

75-87 Kg paste fraction IV.1 was thawed by re-suspending the paste in 1750 liter of pure (injection grade) water. The pH of the suspension was adjusted to 8.95-9.45 with 0.5M NaOH, and the solution was then treated with Aerosil. The Aerosil was added at 7.8-8.2% w/w paste, and the suspension was incubated for 90-110 min at 38° C. Before pursuing to treatment with ethylene glycol, the suspension was cooled to 20-25° C., and the pH was lowered to 5.7-6.3 with about 3% of acetic acid. After the addition of PEG 4000 to 10.5-11.5% w/v, the conductivity was adjusted to 2.7-3.3 mS with NaCl. The suspension was centrifuged at 350-450 liter per hour in a Westfalia Self Desludging centrifuge. The sludge was discarded; the supernatant was filtered through a 1 µm depth filter and loaded on DEAE Sepharose fast flow anion-exchange column equilibrated with sodium acetate solution at pH of 5.9-6.0 and at conductivity of 2.9-3.1 mS. The column was then washed with sodium acetate solution at pH 5.9-6.0, conductivity 2.0-2.1 mS, followed by a wash with Na-acetate at pH 5.9-6.0, conductivity 2.9-3.1. The transferrin-containing protein was collected from the beginning of the first peak until the second peak reached its top. Sodium acetate and 5% acetic acid were added at 9.5 g/l and 41 ml/l, respectively, the pH was adjusted to 5.4-5.5 and conductivity to 7.9-8.1 mS with acetic acid and/or sodium hydroxide.

After the anion-exchange chromatography, the transferrin-containing solution was subjected to a cation exchange column wherein the transferrin was adsorbed onto the cation-exchange resin, and was then eluted by a salt-containing solution. The cation exchange resin was CM-Sepharose fast flow, equilibrated with Na acetate at pH 5.3-5.4, conductivity 0.9-1.0 mS. The transferrin-containing solution was then loaded, the column was washed with Na acetate at pH 5.3-5.4, conductivity 0.9-1.0 mS, and the protein was eluted with Na acetate at pH 6.1-6.3, conductivity 8.8-9.0 mS, until the $OD_{280}$ droped below 25% of the peak height value. After purifying the transferrin, an iron-saturation step was employed. The solution pH was adjusted to 7.5-7.8 by 0.1 M NaOH. Sodium bicarbonate in pure (injection grade) water was added to a final concentration of 10 mM, and $FeCl_3$ was added to a final concentration of 1.7 mg $Fe^{+3}$/g protein. The solution was incubated for 15 min under stirring; the solution pH was then adjusted to 5.9-6.1 and its conductivity to 2.9-3.1 mS with 5% acetic acid, and it was incubated for additional 15 min.

The iron-treated solution was loaded on a second DEAE Sepharose fast flow anion-exchange column. The column was washed with sodium acetate solution at pH of 3.7-4.3 and conductivity of 9.0-12.0 mS, then equilibrated by sodium acetate solution at pH of 7.2-7.6 and conductivity of 9.8-10.1 mS, and followed by equilibration with sodium acetate solution at pH of 7.2-7.6 and conductivity of 2.9-3.1 mS. The iron-treated solution was loaded onto the DEAE column; the column was washed with sodium acetate solution at pH 7.2-7.6, conductivity 1.4-1.6 mS, until the first $OD_{280}$ peak was close to its baseline. The transferrin-containing protein was eluted with Na acetate at pH 7.35-7.45, conductivity 4.9-5.1 mS; collection started as soon as the $OD_{280}$ peak appeared until the OD drops to 12% of the peak height value. The transferrin-containing eluate was now ready for preparation of ultrapure, sterile transferrin products.

Example 3

Preparation of a Pathogen-Free Product

Prior to sterilization, the purified, iron-saturated transferrin solution, obtained either from Cohn's fraction IV.4 or IV.1, should be concentrated. Concentration was performed by ultrafiltration through 10 kD Millipore filter equipped with 6 µM Pall pre filter, until the solution reached 8-10 kg (approximately 15% of its original volume). The sterilization step was performed by filtering the concentrated solution through 0.2 µm sterile filter followed by 0.1 µm sterile filter. Virus inactivation was performed by pasteurizing the filter-sterilized solution at 59.5-60.5° C. for 10.5-11.5 h. After lyophilization and obtaining the final product as described herein below, a total aerobic plate count was performed. Colony forming units was at the range of <7 CFU/g (See example 1 herein above). Bacterial endotoxin should not exceed 1 EU/mg, usually found in the range of <0.005 EU/mg (see example 1 herein above). No mycoplasma growth should be obtained after 4 weeks under enabling growth conditions, as indeed obtained (see example 1 herein above). After sterilization, the ultrapure transferrin product can be subjected to lyophilization, or kept in solution. Total aerobic count, mycoplasma and bacterial endotoxins may be measured by any of the common methods known in the art.

It is possible to perform additional virus inactivation steps involving alternative means for viral inactivation either prior to or following the pasteurization, depending on the requirements of regulatory authorities.

Example 4

Producing Iron-Free Apo-Transferrin

The first product to be obtained is iron saturated, holo-transferrin. Iron free apo-transferrin was obtained by the following method:

The pasteurized iron-saturated transferrin solution was diafiltered through a 10 kD Millipore filter equipped with a 6 µm Pall pre-filter against 200 mM Na citrate, pH 4.4-4.5, until the iron concentration was ≦0.03 mg Fe/mg protein. The solution pH was adjusted to 7.5-7.7 by 0.1 M NaOH, and the solution was diluted to 90 kg by pure (injection grade) water. The solution was further diafiltered against pure (injection grade) water until conductivity is <1 mS and the sodium concentration was less than 10 mEq/ml, and concentrated by ultrafiltration as in example 3 herein above, to reach 20 kg. The resulted solution was sterilized again by filter-sterilization as described in example 3 herein above.

Example 5

Preparation of Conjugates

Conjugate preparation is performed by any suitable method known in the art. The procedure described herein, for conjugation of transferrin with the cytotoxic drug adriamycin is given as a non-limiting example.

Ten mg of transferrin and 3 mg of adriamycin hydrochloride in 1 ml of 0.1 M phosphate buffered saline (PBS), pH 7.0, is added drop wise to 0.5 ml of an aqueous solution of 0.25% glutaraldehyde at room temperature with gentle mixing. After 2 h incubation at room temperature in the dark, 0.5 ml of 1M ethanolamine, pH 7.4, is added and the solution is incubated at 4° C. overnight The mixture is centrifuged at 1,000 g for 15 min and the supernatant is collected. It is then chromatographed through a column of Sepharose CL-6B, equilibrated in 0.16M PBS, pH 7.2. Protein and is identified by peaks that appears at $OD_{280}$ and adriamycin is identified by spectrophotometric reading at $OD_{495}$. The relevant 1.2 ml fractions are pooled and sterilized, preferably by Gamma irradiation. The samples can be stored at 4° C. in the dark.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention. Thus the expressions "means to . . . " and "means for . . . ", or any method step language, as may be found in the specification above and/or in the claims below, followed by a functional statement, are intended to define and cover whatever chemical structure, or whatever function, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. Ultrapure plasma-derived human transferrin which is at least 99% pure, defined as transferrin of the total protein content, and that has an iron binding capacity of at least 1.0 mg per gram of protein, is non-pyrogenic and is pathogen free.

2. The ultrapure transferrin of claim 1, wherein the transferrin is at least 99.1% to at least 99.5% pure.

3. The ultrapure transferrin of claim 1, wherein the ultrapure transferrin is negative for IgG, as determined by binding to anti Ig antibodies in 2% solution.

4. The ultrapure transferrin of claim 1, wherein the ultrapure transferrin is non-reactive with anti-bovine transferrin antibodies and reactive with anti-human transferrin antibodies.

5. The ultrapure transferrin of claim 1, wherein the ultrapure transferrin is free of mycoplasma.

6. The ultrapure transferrin of claim 1, wherein the ultrapure transferrin is iron saturated holo-transferrin, having total bound iron of at least 1.2 mg iron per gram protein.

7. The ultrapure transferrin of claim 1, wherein the ultrapure transferrin is lyophilized.

8. An aqueous solution comprising water and 5% transferrin according to claim 1.

9. The ultrapure transferrin of claim 1, which is iron free apo-transferrin, having a total iron bound of no more than 0.03 mg iron per gram protein.

10. The ultrapure transferrin of claim 9, which is lyophilized.

11. A solution comprising water and 5% iron free apo-transferrin according to claim 9.

12. A method of producing the ultrapure human transferrin of claim 1 which comprises:
pre-treating virus-free Cohn's fraction IV.4 for subsequent application on anion exchange chromatography;
subjecting the pre-treated Cohn's fraction IV.4 to a first anion exchange chromatography, under conditions at which the transferrin is adsorbed;
eluting the adsorbed transferrin from the ion-exchange column, followed by concentration and filter sterilizing;
saturating the eluted transferrin with iron to provide iron-containing transferrin;
subjecting the iron-containing transferrin to a second anion exchange chromatography, under conditions at which the transferrin is adsorbed;
eluting the iron-containing transferrin from the ion-exchange column;
concentrating the eluted iron-containing transferrin;
sterilizing the concentrated iron-containing transferrin by filter-sterilization; and
inactivating remaining viruses in the concentrated and sterilized iron-containing transferrin to obtain ultrapure, sterile, non-pyrogenic, virus-free transferrin.

13. The method of claim 12, wherein the Cohn's fraction IV.4 is non-reactive for Hepatitis B surface Antigen (Hbs Ag), antibody to HIV I+II, anti-HCV and Syphilis.

14. The method of claim 13, wherein the pretreatment of Cohn's fraction I.V.4 comprises:
treating Cohn's fraction IV.4 with Aerosil and PEG to form a suspension;
adjusting the pH of the suspension;
heating the suspension;
separating particulate matter from the suspension by centrifugation;
further clarifying the resultant supernatant by filtration;
adjusting the pH of the filtered supernatant for subsequent application onto an anion exchange chromatography.

15. The method of claim 14, wherein the PEG used to treat the Cohn's fraction IV.4 is PEG 4000.

16. The method of claim 14, wherein the pH of the suspension is adjusted to 5.25 to 5.35.

17. The method of claim 14, wherein the suspension is heated to 52 to 54° C. for 3 hr and then cooled to below about 30° C.

18. The method of claim 14, wherein separation centrifugation is performed in a self-desludging centrifuge.

19. The method of claim 14, wherein filtration is performed through a 3 μm filter.

20. The method of claim 14, wherein the pH of the filtered supernatant is adjusted to 5.55 to 5.85.

21. The method of claim 14, wherein the anion exchange chromatography is performed by DEAE Sepharose fast flow chromatography, with the column optionally being equilibrated with sodium acetate.

22. The method of claim 21, wherein the column is equilibrated with a sodium acetate solution at pH and conductivity values that allow transferrin to adsorb to the DEAE Sepharose.

23. The method of claim 21, wherein the column is eluted with a sodium acetate solution at pH and conductivity values adequate for transferrin elution from the DEAF Sepharose.

24. The method of claim 14, wherein concentration is performed by ultra-filtration.

25. The method of claim 14, wherein the iron used to saturate the transferrin is $FeCl_3$ to reach an iron concentration of about 1.7 mg $Fe^{+3}$/mg protein.

26. The method of claim 14, wherein virus inactivation comprises pasteurization.

27. The method of claim 26, wherein virus inactivation further comprises detergent inactivation or nanofiltration.

28. A method of producing the ultrapure human transferrin of claim 1 in the form of ultrapure iron-saturated (holo-) transferrin, which method comprises:
   pre-treating virus-free Cohn's fraction IV. 1 for subsequent application on ion exchange chromatography;
   subjecting the pre-treated Cohn's fraction IV. 1 to a first anion exchange chromatography;
   collecting transferrin solution from the anion-exchange column;
   subjecting the collected transferrin solution to cation-exchange chromatography;
   eluting the transferrin from the cation-exchange column;
   saturating the transferrin with iron;
   subjecting the iron-saturated transferrin to a second anion exchange chromatography, under conditions in which the transferrin is adsorbed;
   eluting transferrin from the ion-exchange medium;
   concentrating the eluted transferrin;
   sterilizing the concentrated transferrin-containing eluate by filter-sterilization;
   inactivating remaining viruses to obtain ultrapure, sterile, non-pyrogenic, virus-free transferrin.

29. The method of claim 28, wherein the Cohn's fraction IV. 1 is non-reactive for Hepatitis B surface Antigen (Hbs Ag), antibody to HIV I+II, anti-HCV and Syphilis.

30. The method of claim 28, wherein the pre-treatment of Cohn's fraction IV. 1 comprises:
   diluting the Cohn's fraction IV. 1 with pure water to form a suspension;
   treating the Cohn's fraction IV. 1 in the suspension with Aerosil and PEG;
   adjusting the pH and conductivity of the treated suspension for subsequent application onto anion exchange chromatography;
   removing particulate matter from the suspension by separation centrifugation; and
   further clarifying the supernatant by filtration.

31. The method of claim 30, wherein the Cohn's fraction IV. 1 is treated with PEG 4000.

32. The method of claim 30, wherein the pH of the suspension is adjusted to 5.7 to 6.3, and the conductivity is adjusted to 2.7 to 3.3 mS.

33. The method of claim 30, wherein separation of particulate matter is performed by self-desludging centrifugation.

34. The method of claim 30, wherein filtration is performed through a 1 μm filter.

35. The method of claim 30, wherein the anion exchange chromatography is performed with DEAE Sepharose fast flow chromatography.

36. The method of claim 35, wherein the column is washed with a sodium acetate solution at pH and conductivity values allowing transferrin to be washed from the DEAE Sepharose.

37. The method of claim 36 wherein the sodium acetate solution has a pH of 5.9 to 6.0 and a conductivity of 2.7 to 3.3.

38. The method of claim 30, wherein the cation exchange chromatography is performed on CM-Sepharose, with the column optionally being equilibrated with sodium acetate.

39. The method of claim 38, wherein the sodium acetate solution is at pH and conductivity values allowing transferrin to adsorb to the CM Sepharose.

40. The method of claim 39, wherein the column is eluted with a sodium acetate solution at pH and conductivity values adequate for transferrin elution from the CM Sepharose.

41. The method of claim 30, wherein concentration is performed by ultra-filtration.

42. The method of claim 30, wherein the iron used to saturate the transferrin is $FeCl_3$ to reach an iron concentration of about 1.7 mg $Fe^{+3}$/mg protein.

43. The method of claim 30, wherein virus inactivation comprises pasteurization.

44. The method of claim 43, wherein virus inactivation further comprises detergent inactivation or nanofiltration.

45. A method for producing the ultrapure human transferrin of clam 1 in the form of ultrapure iron-free (apo-) transferrin, which method comprises:
   providing ultrapure iron-saturated holo-transferrin;
   diafiltering the iron-saturated transferrin solution for iron removal to form an iron-free solution;
   concentrating the resultant iron-free solution; and
   sterilizing the ultrapure, iron-free transferrin.

46. The method of claim 45, wherein diafiltration is performed against sodium citrate.

47. The method of claim 45, wherein concentration is performed by ultra-filtration.

48. The method of claim 45, wherein sterilization is performed by filtration.

49. A pharmaceutical composition comprising ultrapure transferrin according to claim 1 in combination with a pharmaceutically acceptable excipient, diluent or carrier, wherein the transferrin constitutes at least 99% of the total protein content in said composition.

50. A pharmaceutical composition comprising a covalent conjugate between a bioactive moiety and ultrapure, plasma-derived human transferrin
   wherein the conjugate is at least 99% pure, wherein purity is defined as
   transferrin of the total protein content in said pharmaceutical composition, wherein the conjugate has an iron binding capacity of at least 1.0 mg/g of protein, is non-pyrogenic and is pathogen free, wherein the bioactive moiety is selected from the group consisting of a cytotoxic compound, a cytostatic compound, an antisense compound, an anti-viral agent, a specific antibody, and an imaging agent, and wherein said pharmaceutical composition further comprises a pharmaceutically acceptable carrier.

* * * * *

UNITED STATES PATENT AND TRADEMARK OFFICE
CERTIFICATE OF CORRECTION

PATENT NO. : 7,285,646 B2  Page 1 of 1
APPLICATION NO. : 10/964394
DATED : October 23, 2007
INVENTOR(S) : Bauer It is certified that error appears in the above-identified patent and that said Letters Patent is hereby corrected as shown below:

Column 15
Line 41 (claim 1, line 4), change "mg-per" to -- mg per --.

Column 16
Line 28 (claim 14, line 2), change "LV.4" to -- IV.4 --.
Line 62 (claim 23, line 3), change "DEAF" to -- DEAE --.

Column 17
Line 41 (claim 30, last line), change "supematant" to -- supernatant --.

Column 18
Line 23 (claim 45, line 2), change "clam" to -- claim --.
Line 46 (claim 50, line 5), after "is defined as", insert the paragraph beginning with "transferring" and ending with "composition,".
Line 48 (claim 50, line 7), after "composition," begin a new paragraph with "wherein".
Line 50 (claim 50, line 9), after "free," begin a new paragraph with "wherein".
Line 54 (claim 50, line 13), after "agent," begin a new paragraph with "and wherein".

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,285,646 B2  
APPLICATION NO. : 10/964394  
DATED : October 23, 2007  
INVENTOR(S) : Bauer It is certified that error appears in the above-identified patent and that said Letters Patent is hereby corrected as shown below:

Column 15  
Line 41 (claim 1, line 4), change "mg-per" to -- mg per --.

Column 16  
Line 28 (claim 14, line 2), change "LV.4" to -- IV.4 --.  
Line 62 (claim 23, line 3), change "DEAF" to -- DEAE --.

Column 17  
Line 41 (claim 30, last line), change "supematant" to -- supernatant --.

Column 18  
Line 23 (claim 45, line 2), change "clam" to -- claim --.  
Line 46 (claim 50, line 5), after "is defined as", insert the paragraph beginning with --transferring-- and ending with -- composition, --.  
Line 48 (claim 50, line 7), after "composition," begin a new paragraph with -- wherein --.  
Line 50 (claim 50, line 9), after "free," begin a new paragraph with -- wherein --.  
Line 54 (claim 50, line 13), after "agent," begin a new paragraph with -- and wherein --.

Signed and Sealed this

Eighth Day of January, 2008

JON W. DUDAS  
*Director of the United States Patent and Trademark Office*